United States Patent
Ozawa et al.

(10) Patent No.: US 9,446,254 B2
(45) Date of Patent: Sep. 20, 2016

(54) CHARGER ALIGNMENT IN AN IMPLANTABLE MEDICAL DEVICE SYSTEM EMPLOYING REFLECTED IMPEDANCE MODULATION

(75) Inventors: Robert Ozawa, Woodland Hills, CA (US); Daniel Aghassian, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 143 days.

(21) Appl. No.: 13/608,600

(22) Filed: Sep. 10, 2012

(65) Prior Publication Data
US 2013/0096651 A1   Apr. 18, 2013

Related U.S. Application Data

(60) Provisional application No. 61/546,850, filed on Oct. 13, 2011.

(51) Int. Cl.
*A61N 1/378* (2006.01)
*H02J 5/00* (2016.01)
(Continued)

(52) U.S. Cl.
CPC ..... *A61N 1/3787* (2013.01); *A61F 2250/0001* (2013.01); *A61N 1/08* (2013.01); *A61N 1/37252* (2013.01); *H02J 5/005* (2013.01); *H02J 7/025* (2013.01)

(58) Field of Classification Search
CPC .. A61N 1/3787; A61N 1/37252; A61N 1/08; A61F 2250/0001; H02J 7/025; H02J 5/005
USPC ............... 607/32, 33, 42, 60, 61, 65
See application file for complete search history.

(56) References Cited

U.S. PATENT DOCUMENTS 3,942,535 A   3/1976   Schulman
6,516,227 B1  2/2003   Meadows et al.
(Continued)

FOREIGN PATENT DOCUMENTS

JP   2003-348774 A   12/2003

OTHER PUBLICATIONS

U.S. Appl. No. 61/414,616, filed Nov. 17, 2010, Carbunaru, et al.
(Continued)

*Primary Examiner* — Christopher D Koharski
*Assistant Examiner* — Pamela M Bays
(74) *Attorney, Agent, or Firm* — Lewis, Reese & Nesmith, PLLC

(57) ABSTRACT

The disclosed means of determining alignment between an external charger and an implantable medical device (IMD) involves the use of reflected impedance modulation, i.e., by measuring at the external charger reflections arising from modulating the impedance of the charging coil in the IMD. During charging, the charging coil in the IMD is pulsed to modulate its impedance. The difference in the coil voltage (ΔV) produced at the external charger as a result of these pulses is assessed and is used by the external charger to indicate coupling. If the magnitude of ΔV is above a threshold, the external charger considers the coupling to the IMD to be adequate, and an alignment indicator in the external charger is controlled accordingly. The magnitude of Vcoil can be assessed in addition to ΔV to determine alignment with the IMD with improved precision, and/or to further define a high quality alignment condition.

16 Claims, 12 Drawing Sheets

(51) Int. Cl.
*H02J 7/02* (2016.01)
*A61N 1/08* (2006.01)
*A61N 1/372* (2006.01)

(56) References Cited

U.S. PATENT DOCUMENTS

| | | | |
|---|---|---|---|
| 2006/0069412 A1* | 3/2006 | Ginggen et al. | 607/33 |
| 2006/0247737 A1* | 11/2006 | Olson et al. | 607/61 |
| 2008/0172109 A1 | 7/2008 | Rahman et al. | |
| 2009/0118796 A1 | 5/2009 | Chen et al. | |
| 2010/0010582 A1* | 1/2010 | Carbunaru et al. | 607/61 |
| 2010/0137948 A1 | 6/2010 | Aghassian et al. | |
| 2010/0204756 A1 | 8/2010 | Aghassian | |
| 2010/0222848 A1* | 9/2010 | Forsell | 607/61 |
| 2011/0004278 A1 | 1/2011 | Aghassian et al. | |
| 2011/0046699 A1 | 2/2011 | Mazanec | |
| 2011/0087307 A1 | 4/2011 | Carbunaru et al. | |
| 2011/0093048 A1 | 4/2011 | Aghassian | |
| 2011/0112610 A1 | 5/2011 | Rahman et al. | |
| 2011/0112611 A1 | 5/2011 | Aghassian | |
| 2011/0196452 A1 | 8/2011 | Forsell | |
| 2011/0276111 A1 | 11/2011 | Carbunaru et al. | |
| 2012/0119699 A1 | 5/2012 | Carbunaru et al. | |

OTHER PUBLICATIONS

U.S. Appl. No. 61/546,871, filed Oct. 13, 2011, Ozawa.
International Search Report and Written Opinion regarding PCT Application No. PCT/US2012/057582 dated Dec. 13, 2012.

* cited by examiner

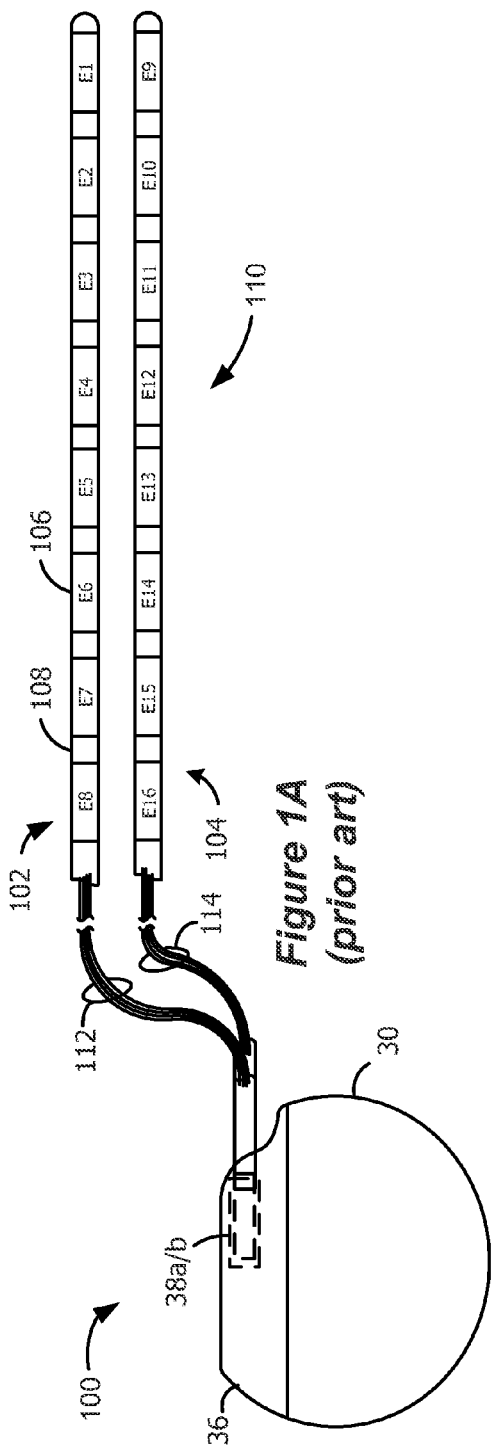
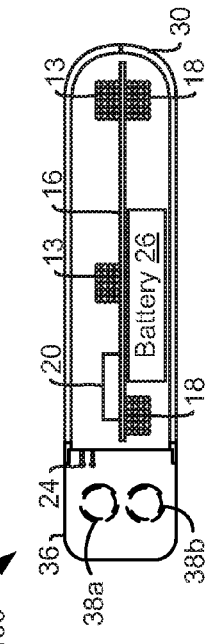
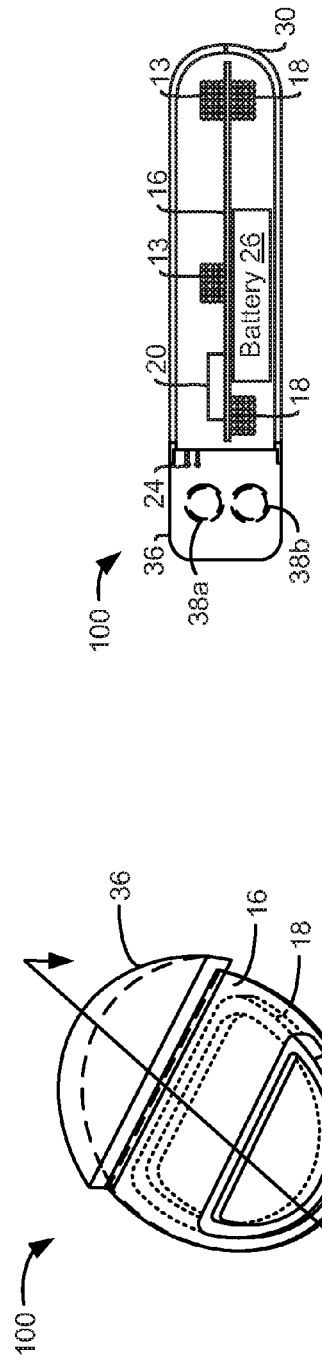

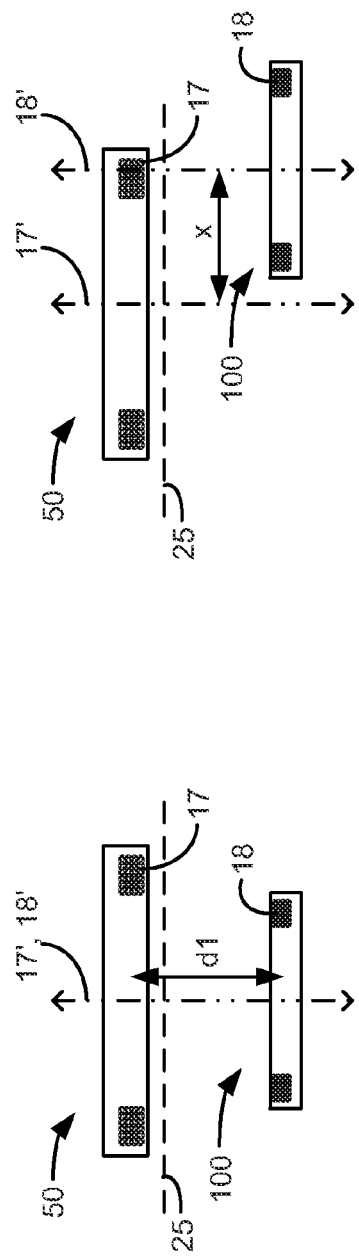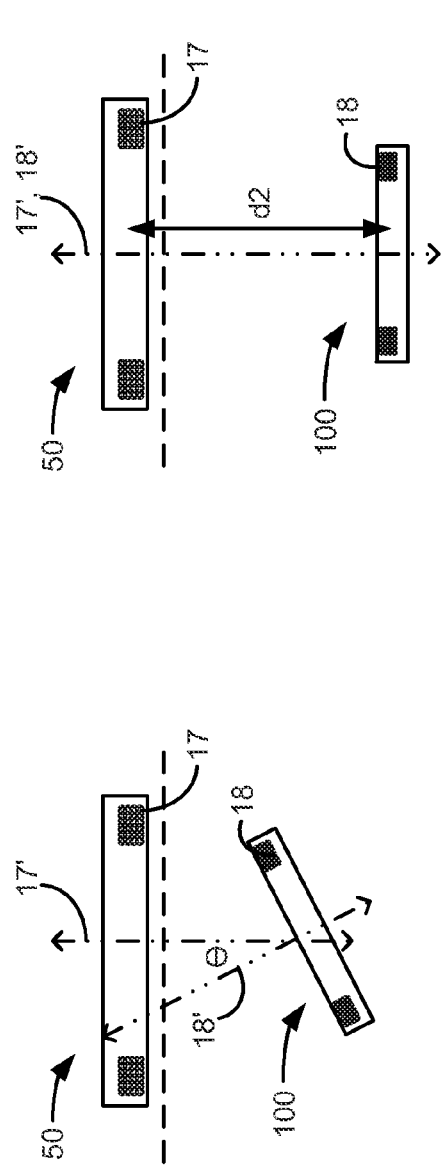

CHARGER ALIGNMENT IN AN IMPLANTABLE MEDICAL DEVICE SYSTEM EMPLOYING REFLECTED IMPEDANCE MODULATION

CROSS REFERENCE TO RELATED APPLICATIONS

This is a non-provisional filing of U.S. Provisional Patent Application Ser. No. 61/546,850, filed Oct. 13, 2011, which is incorporated herein and to which priority is claimed.

This application is related to a U.S. Provisional Patent Application Ser. No. 61/546,871, filed Oct. 13, 2011.

FIELD OF THE INVENTION

The present invention relates to wireless external chargers for use in implantable medical device systems.

BACKGROUND

Implantable stimulation devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder sublaxation, etc. The description that follows will generally focus on the use of the invention within a Spinal Cord Stimulation (SCS) system, such as that disclosed in U.S. Pat. No. 6,516,227. However, the present invention may find applicability in any implantable medical device system.

As shown in FIGS. 1A-1C, a SCS system typically includes an Implantable Pulse Generator (IPG) 100, which includes a biocompatible device case 30 formed of a conductive material such as titanium for example. The case 30 typically holds the circuitry and battery 26 necessary for the IPG to function, although IPGs can also be powered via external RF energy and without a battery. The IPG 100 is coupled to electrodes 106 via one or more electrode leads (two such leads 102 and 104 are shown), such that the electrodes 106 form an electrode array 110. The electrodes 106 are carried on a flexible body 108, which also houses the individual signal wires 112 and 114 coupled to each electrode. In the illustrated embodiment, there are eight electrodes on lead 102, labeled $E_1$-$E_8$, and eight electrodes on lead 104, labeled $E_9$-$E_{16}$, although the number of leads and electrodes is application specific and therefore can vary. The leads 102, 104 couple to the IPG 100 using lead connectors 38a and 38b, which are fixed in a non-conductive header material 36, which can comprise an epoxy for example.

As shown in the cross-section of FIG. 1C, the IPG 100 typically includes an electronic substrate assembly including a printed circuit board (PCB) 16, along with various electronic components 20 mounted to the PCB 16, some of which are discussed subsequently. Two coils (more generally, antennas) are generally present in the IPG 100: a telemetry coil 13 used to transmit/receive data to/from an external controller (not shown); and a charging coil 18 for charging or recharging the IPG's battery 26 using an external charger 50 (discussed further below). In this example, the telemetry coil 13 and charging coil 18 are within the case 30, as disclosed in U.S. Patent Publication 2011/0112610. (FIG. 1B shows the IPG 100 with the case 30 removed to ease the viewing of the two coils 13 and 18). However, the telemetry coil 13 may also be mounted within the header 36 of the IPG 100 (not shown).

FIG. 2 shows the IPG 100 in communication with external charger 50 just mentioned. The external charger 50 is used to wirelessly convey power to the IPG 100, which power can be used to recharge the IPG's battery 26. The transfer of power from the external charger 50 is enabled by a coil (antenna) 17. The external charger 50, like the IPG 100, also contains a PCB 70 on which electronic components 72 are placed. Again, some of these electronic components 72 are discussed subsequently. A user interface 74, including touchable buttons and perhaps a display and a speaker, allows a patient or clinician to operate the external charger 50. A battery 76 provides power for the external charger 50, which battery 76 may itself be rechargeable. The external charger 50 can also receive AC power from a wall plug. A handholdable case 77 sized to fit a user's hand contains all of the components.

Power transmission from the external charger 50 to the IPG 100 occurs wirelessly, and transcutaneously through a patient's tissue 25, via inductive coupling. FIG. 3 shows details of the circuitry used to implement such functionality. Coil 17 in the external charger 50 is energized via charging circuit 122 with a constant non-data-modulated AC current, Icharge, to create an AC magnetic charging field. This magnetic field induces a current in the charging coil 18 within the IPG 100, which current is rectified (132) to DC levels, and used to recharge the battery 26, perhaps via a charging and battery protection circuit 134 as shown. The frequency of the magnetic charging field can be perhaps 80 kHz or so. When charging the battery 26 in this manner, is it typical that the case 77 of the external charger 50 touches the patient's tissue 25, although this is not strictly necessary.

The IPG 100 can also communicate data back to the external charger 50 during charging using reflected impedance modulation, which is sometimes known in the art as Load Shift Keying (LSK). Such back telemetry from the IPG 100 can provide useful data concerning charging to the external charger 50, such as the capacity of the battery 26, or whether charging is complete and the external charger 50 can cease.

Control circuitry 140 in the IPG 100 monitors the battery voltage, Vbat, and with the assistance of LSK module 155, produces LSK data. The control circuitry 140 can include a microcontroller for example, and may be associated with Analog-to-Digital (A/D) conversion circuitry to process and interpret the battery voltage. LSK module 155 preferably operates as software in the control circuitry 140, and assesses the incoming battery voltage to produce appropriate LSK data at appropriate times. Such LSK data is sent as a serial string of bits along line 99 to the gates of load transistors 141 and 142. The LSK data modulates the state of transistors 141 and 142, which in turn modulates the impedance of the coil 18. When LSK data=1, the transistors 141 and 142 are on (shorted) which shorts each end of the coil 18 to ground. When LSK data=0, the transistors are off (opened). The impedance of the coil 18 may also be modulated by a single transistor in series with the coil 18, which modulates the impedance by opening the coil, as shown in dotted lines.

Such modulation of the charging coil 18 is detectable at the external charger 50. Due to the mutual inductance between the coils 17 and 18, any change in the impedance of coil 18 affects the voltage needed at coil 17, Vcoil, to drive the charging current, Icharge: if coil 18 is shorted (LSK data=1), Vcoil increases to maintain Icharge; if not shorted (LSK data=0), Vcoil decreases. In this sense, the impedance modulation of coil 18 is "reflected" back to the transmitting coil 17, and thus data can be said to be "transmitted" from the IPG 100 to the external charger 50, even if not transmitted in the traditional sense. An example Vcoil waveform arising from transmission of an example sequence (LSK data=01010) is shown at the bottom of FIG. 3, and shows the data states as modulated by the ~80 kHz frequency of the magnetic field.

The Vcoil waveform is processed at demodulation circuitry 123 to recover the transmitted LSK data. To be reliably detected, the difference in coil voltage ($\Delta V$) between the transmitted '0' ($Vcoil_0$) and '1' ($Vcoil_1$) states must as a practical matter be greater than a threshold voltage inherent in the demodulator 123, Vt1. Depending on the particularly of the circuitry, Vt1 can be rather small, ranging from 50 mV to 100 mV for instance, and can be statistically determined based on suitable bit error rates for LSK transmission.

The serial stream of demodulated bits is then received at control circuitry 144 operating in the external charger 50, so that appropriate action can be taken. The control circuitry 144 can again include a microcontroller for example. For example, if an alternating stream of bits is received (01010101 . . . ), this might be interpreted by the control circuitry 144 that the battery 26 in the IPG 100 is full, and therefore that charging can cease. In such an instance, the control circuitry 144 can suspend the production of the magnetic charging field (i.e., setting Icharge to 0), and may notify the user of that fact (by a graphical display, an audible beep, or other indicator).

Because LSK telemetry works on a principle of reflection, LSK data can only be communicated from the IPG 100 to the external charger 50 during periods when the external charger is active and is producing a magnetic charging field.

An issue arising when inductive coupling is used for power transmission relates to the coupling between the coils 17 and 18 in external charger 50 and the IPG 100. Coupling, generally speaking, comprises the extent to which power expended at the transmitting coil 17 in the external charger 50 is received at the coil 18 in the IPG 100. It is generally desired that the coupling between coils 17 and 18 be as high as possible: higher coupling results in faster charging of the IPG battery 26 with the least expenditure of power in the external charger 50. Poor coupling is disfavored, as this will require high power drain (i.e., a high Icharge) in the external charger 50 to adequately charge the IPG battery 26. The use of high power depletes the batteries 76 (if any) in the external charger 50, and more importantly can cause the external charger 50 to heat up, and possibly burn or injure the patient.

Coupling depends on many variables, such as the permeability of the materials used in the external charger 50 and the IPG 100, as well materials inherent in the environment. Coupling is also affected by the relative positions of the external charger 50 and IPG 100, as shown in FIGS. 4A-4D. For best coupling, it is preferred that axes around which coils 17 and 18 are wound (17' and 18') are parallel and collinear, and that the coils 17 and 18 as close as possible (d1) to each other, as shown in FIG. 4A. Distance d1 indicates the depth between the external charger 50 and the IPG 100, and is generally constant given that the external charger is generally placed on the patient's tissue 25, and that the IPG 100 has been implanted at a particular depth. Deviations from these ideal conditions will generally reduce coupling, as shown in FIGS. 4B-4D. In FIG. 4B for instance, the coil axes 17' and 18' are not collinear, but instead are laterally offset (x). In FIG. 4C, the coil axes 17' and 18' are not parallel, but instead have an angle $\Theta$ between them. In FIG. 4D, the coil axes 17' and 18 are parallel and collinear, but the IPG 100 is relatively deep (d2).

In any of these non-ideal cases 4B-4D, coupling will be reduced, meaning that the external charger 50 must output more power (e.g., Icharge must be higher) to affect the same charging rate of the IPG's battery 26. Some of these non-idealities cannot be avoided after implantation: for example, if the IPG 100 is deeply implanted (FIG. 4D), or implanted at an angle (FIG. 4C), poor coupling with the external charger 50 may be unavoidable.

However, poor lateral placement (FIG. 4B) can be improved by the user by moving the external charger 50 into better alignment with the IPG 100 during production of the magnetic charging field. In this regard, the art has taught different means of detecting and indicating such lateral misalignment to the user. Generally, the control circuitry 144 in the external charger 50 indicates misalignment to a user via an alignment indicator 162. Often, the alignment indicator 162 comprises a speaker for issuing an audible indication such as a "beep" for example when the external charger 50 is misaligned with the IPG 100. (Alternately, a "beep" could indicate an aligned condition). Alignment indicator 162 can also comprise a visual indicator such as a display or a lamp (e.g., an LED) on the external charger 50, or a tactile indicator such as a vibration motor that causes the external charger 50 to vibrate. (An audible or tactile indication would be preferred if the external charger 50 isn't easily viewed by the patient during a charging session). Upon hearing, seeing, or feeling (or failing to see, hear, or feel) such an indication, the user of the external charger 50 can use his or her hand to then laterally shift the position of the external charger 50 around until better alignment is achieved, and the indicator ceases (or issues).

However, many prior alignment approaches are complicated, requiring significant and expensive modifications to the external charger 50. For example, in some techniques, information relevant to coupling is telemetered from the implant to the external charger 50. Such information may comprise an indication of the rate at which the battery 26 in the IPG is being charged, such as the current flowing into the battery 26, Ibat. However, because the magnetic charging field is relatively intense compared to fields typically used to telemeter data and thus could interfere with such telemetry, the external charger 50 must periodically suspend the magnetic charging field to allow the telemetry coupling data to be received from the IPG 100. But suspending the magnetic charging field means that the battery 26 in the IPG 100 is not charged during such times, which can lengthen the charging process. Also, telemetering coupling data requires the external charger 50 to have additional receiver circuitry to receive telemetry in the forms traditionally used by the IPG 100. For example, telemetry to and from the IPG 100 (i.e., to and from the IPG's telemetry coil 13) often occurs in accordance with well-known Frequency Shift Keying (FSK) protocols. Thus, the external charger 50 would need to be designed with FSK receiver circuitry, including error detection schemes, etc. This adds cost and complexity to the external charger 50.

Applicants have come up with a new, simpler means for detecting the alignment between an external charger and an implantable medical device such as an IPG.

BRIEF DESCRIPTION OF THE DRAWINGS

FIGS. 1A-1C show different views of an implantable medical device, specifically an Implantable Pulse Generator (IPG).

FIG. 4 shows alignment and coupling between the IPG and external charger for various orientations.

DETAILED DESCRIPTION

The description that follows relates to use of the invention within a spinal cord stimulation (SCS) system. However, it is to be understood that the invention is not so limited, and could be used with any type of implantable medical device system.

The disclosed means of determining alignment between an external charger and an implantable medical device such as an IPG involves the use of reflected impedance modulation, i.e., by measuring at the external charger reflections arising from modulating the impedance of the charging coil in the IPG. Reflected impedance modulation has been used in legacy systems to enable Load Shift keying (LSK) telemetry to send data to the external charger to control charging, as discussed in the Background. However, the alignment detection method of this disclosure doesn't involve data transmission, although some of the same LSK hardware can be used. During charging, the charging coil in the IPG is periodically pulsed to modulate its impedance. The magnitude of the change in the coil voltage ($\Delta V$) produced at the external charger as a result of these pulses is assessed and is used by the controller circuitry in the external charger as indicative of coupling, and hence to specify an alignment condition. If the magnitude of $\Delta V$ is above a significant threshold, the external charger considers the coupling to the IPG to be adequate, and an alignment indicator in the external charger is controlled accordingly (e.g., by sounding or extinguishing a beep). In a modification to this basic technique, the magnitude of Vcoil can be assessed in addition to $\Delta V$ to determine alignment with the IPG with improved precision, with both parameters being used to define an alignment condition, and/or to further define a high quality alignment condition.

Figure 2:
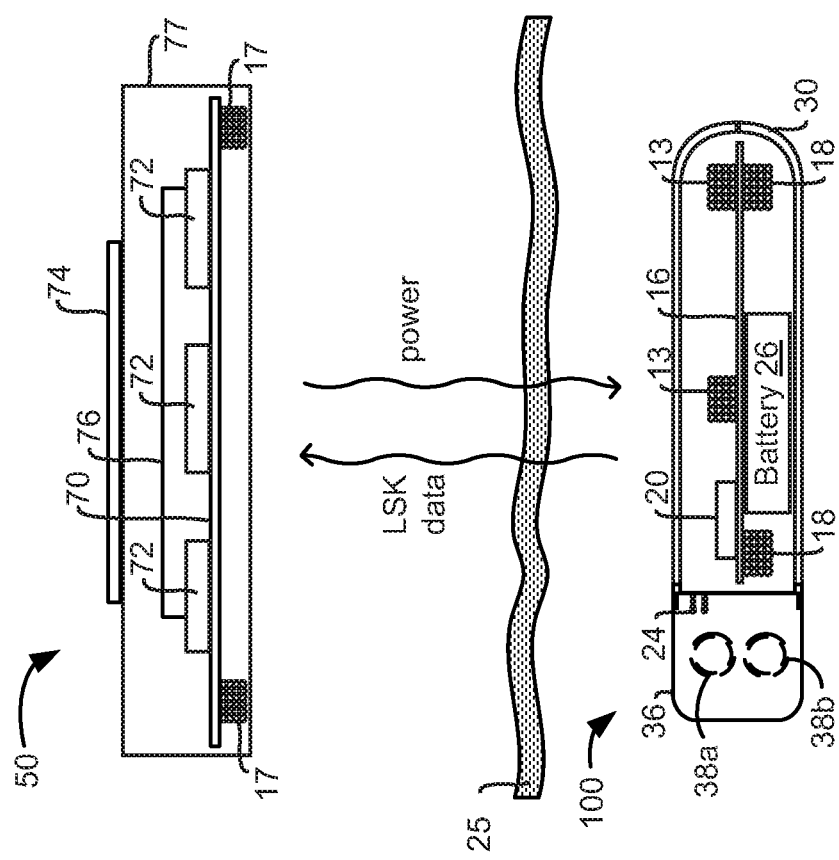
FIG. 2 shows wireless links between the IPG and an external charger.
Figure 3:
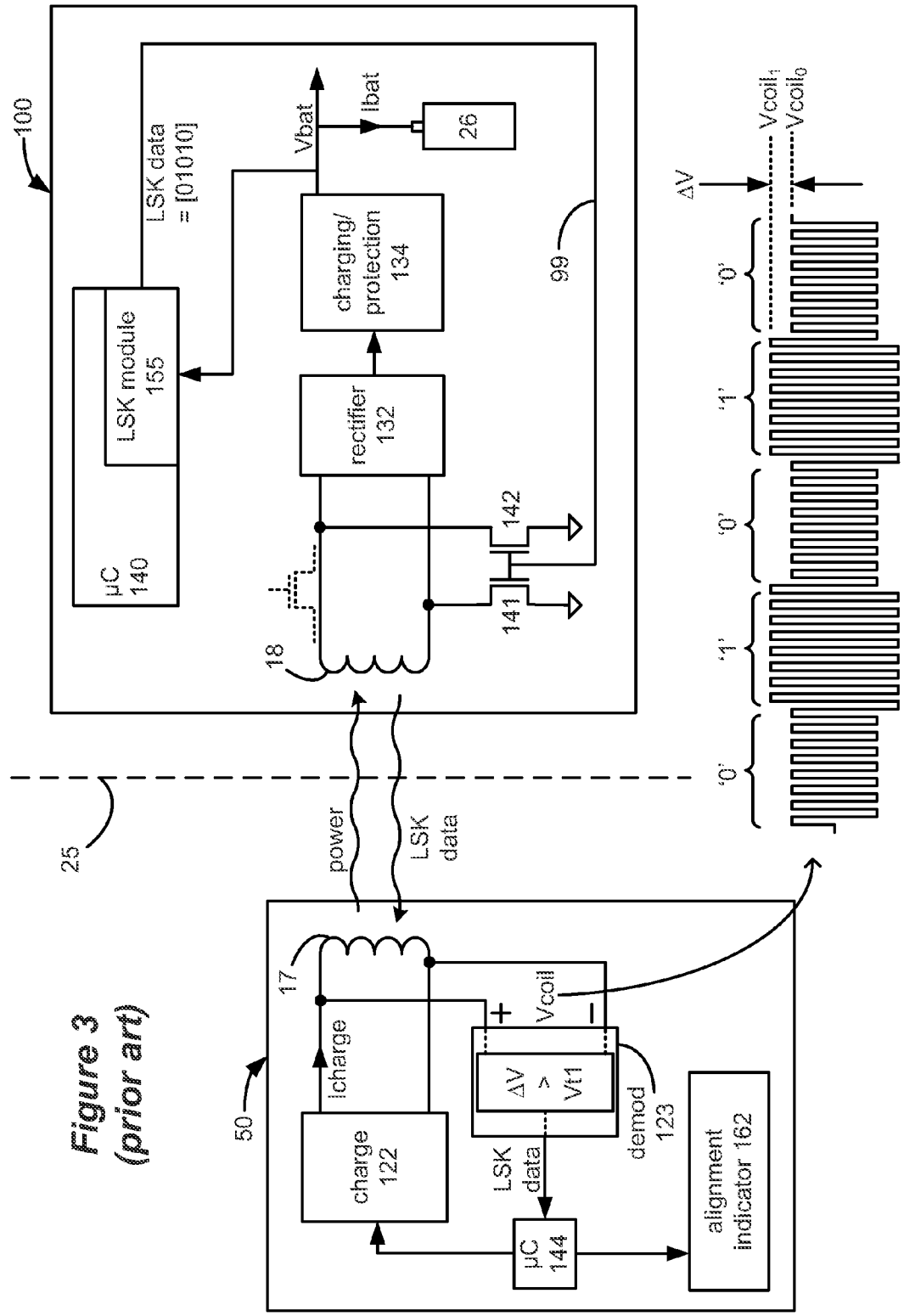
FIG. 3 shows circuitry in both the IPG and external charger for providing power to the IPG, and for telemetering data to the external charger using reflective impedance modulation to control charging.
Figure 5:
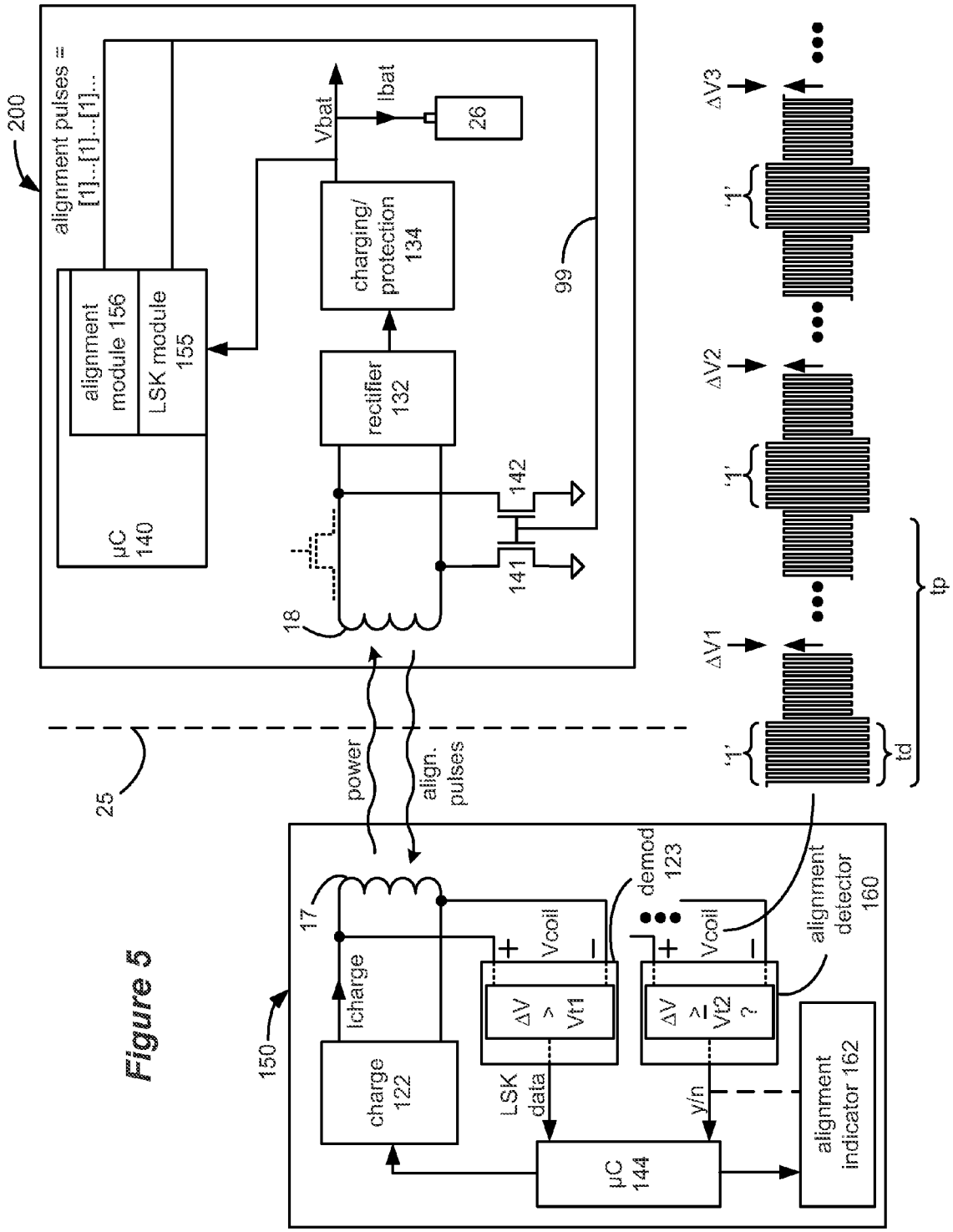
FIG. 5 shows circuitry for an improved IPG/external charger system in which reflected impedance modulation is used to provide alignment information, and in particular the use of a difference in the coil voltage ($\Delta V$) to provide the coupling data indicative of alignment.

An improved external charger 150/IPG 200 system having such functionality is shown schematically in FIG. 5. Starting with the IPG 200, the basic hardware remains unchanged form the IPG 100 discussed earlier. As before, an LSK module 155 monitors the voltage of the battery 26 (Vbat) during charging, and when necessary telemeters LSK data back to the external charger, starting with the issuance of serial data bits on line 99. New to IPG 200 however is an alignment module 156, which like LSK module 155 also preferably operates as software in the control circuitry 140. During reception of a magnetic charging field, the alignment module 156 periodically issues alignment pulses on line 99 to modulate the impedance of the transistors 141 and 142. As shown, these alignment pulses can comprise the periodic issuance of a logic '1' pulse (which shorts the charging coil 18 to ground) followed by an extended period of no pulse (i.e., line 99 is set to '0').

The timing of the alignment pulses can vary, but in one example the alignment pulses have a duration (td) of 2 ms and a period (tp) of 200 ms. Notice that this relationship between td and tp means that the charging coil 18 is only shorted—and hence unable to receive to power for battery recharging—for 1% of the time, which does not significantly extend the time needed to recharge the battery 26. Both of these timing parameters can be modified over the course of a charging session. For example, tp may be relatively short (200 ms) at the beginning of receipt of a magnetic charging field, when a charging session has begun and alignment is probably most needed. However, after some number of seconds suitable to allow for initial alignment adjustment, tp can be increased (e.g., to 1 s), which provides alignment data to the external charger less frequently but which also disturbs power reception less often.

Unlike LSK data, the alignment pulses issued by the alignment module 156 are not data per se. They are only meant to occasionally modulate the impedance of the charging coil 18 for the purpose of creating reflections assessable at the external charger 150 to infer external charger 150/IPG 200 alignment. It is preferred that the alignment pulses be obviously different from the expected structure of LSK data so that they are not misinterpreted at the external charger 150. For example, if normal LSK data to suspend charging comprises alternating logic states (01010 . . . ) as discussed in the Background, then a single alignment pulse followed by a long absence of pulses (effectively, 1000000000 . . . ) is not likely to be misinterpreted at the demodulator 123 as data for controlling the external charger 150.

The reflections produced in Vcoil at the external charger 150 by the alignment pulses are shown in FIG. 5. In this example, Vcoil can as before be assessed at demodulator 123 to decode LSK telemetry, and to control charging accordingly. However, Vcoil is additionally assessed in this embodiment at separate alignment detection circuitry 160. The alignment detection circuitry 160 assesses the magnitude of $\Delta V$, i.e., the difference in voltage between reflected '1' and '0' alignment pulses, and in this embodiment assesses whether this difference is greater than a threshold, Vt2. The inventors have noticed that the magnitude of $\Delta V$ is indicative of the coupling between the coil 17 in the external charger and charging coil 18 in the IPG 200, with $\Delta V$ increasing as coupling improves, and decreasing as coupling worsens. In the example shown, the alignment detector 160 issues yes/no (e.g., binary) alignment data to the control circuitry 144, which in turn controls an alignment indicator 162 similar to that discussed in the Background: for example, upon hearing, seeing, or feeling (or failing to see, hear, or feel) an indication, the user of the external charger 50 can shift the position of the external charger 150 until better alignment is achieved, and the indication ceases (or issues). The alignment detector 160 can also issue its determination directly to the alignment indicator 162, as shown by dotted line in FIG. 5.

The threshold Vt2 used by the alignment detector 160 will generally be a threshold significantly higher than Vt1, i.e., the inherent threshold at which the demodulator 123 can reliably discern between LSK reception of a '0' or '1' logic state. Threshold Vt2 is chosen to guarantee a particular charging rate of the battery 26 in the IPG 200. Although these thresholds are highly dependent on the particular implementation chosen, a Vt2 suitable for use by the alignment detector 160 may range from 150 mV to 300 mV for example.

The detector circuitry 160 may be implemented in any number of ways as one skilled in the art will realize. It may include for example A/D converter circuitry (not shown) for digitally sampling the Vcoil waveform and for processing the result to arrive at accurate $\Delta V$ values. Detector circuitry 160 may average some number of the incoming $\Delta V$ values ($\Delta V1$, $\Delta V2$, $\Delta V3$, etc.) to arrive at a yes/no determination of alignment that is integrated over time, and is thus not as susceptible to "spikes" in the $\Delta V$ data. Alternatively, the digitized values of Vcoil can be sent to the control circuitry 144 for interpretation. The alignment detector 160 can comprise, or be integrated with, the control circuitry 144, which control circuitry 144 can also perform other control functions in the external charger 150 as one skilled in the art will understand. Moreover, although the alignment detector 160 is shown as separate from the demodulator 123 used to discern LSK data, these two circuits blocks can be integrated, at least in part. For example, both the demodulator 123 and the alignment detector 160 can share front end A/D converter circuitry used to sample the Vcoil waveform.

Figure 6:
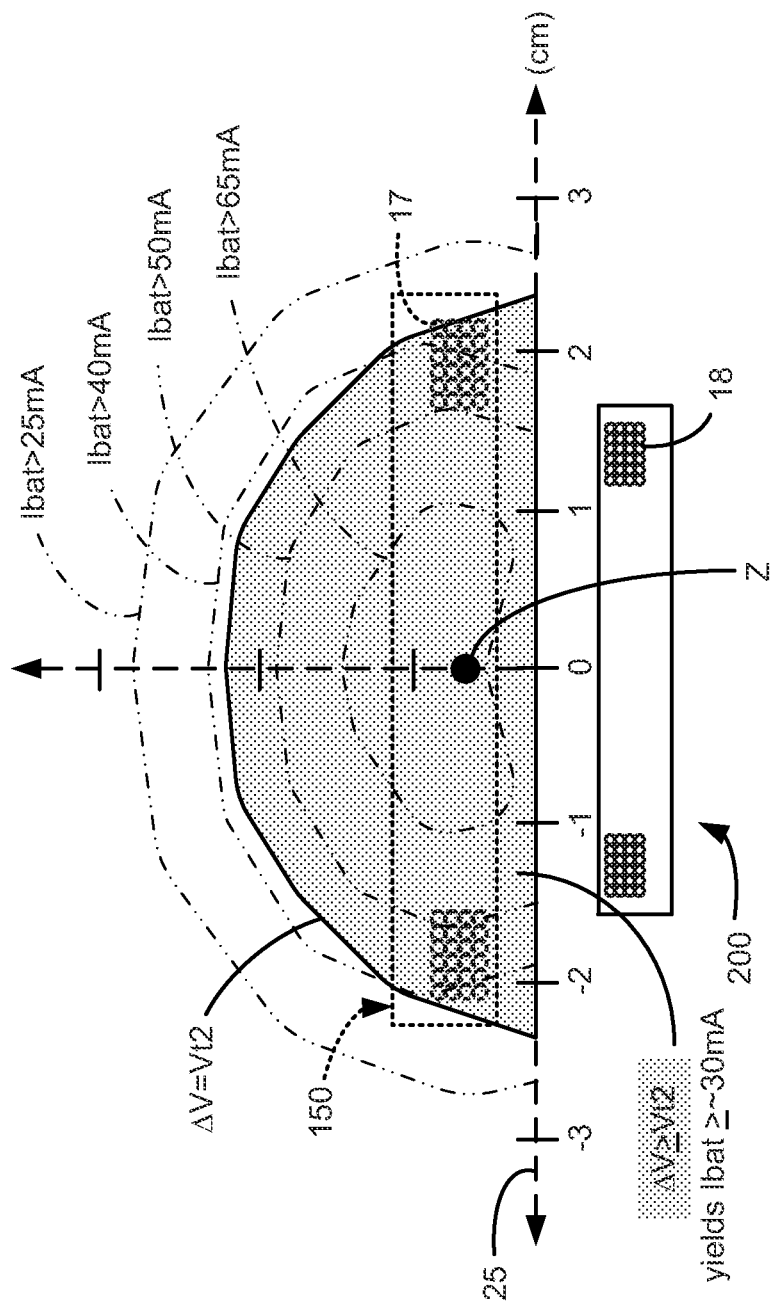
FIG. 6 shows how $\Delta V$ can be used to indicate alignment by utilizing a $\Delta V$ threshold to define a volume having a suitable battery charge rate.

FIG. 6 illustrates bench test data showing how Vt2 can be chosen for use in the alignment detector 160. In this example, it is assumed that the IPG 200 is implanted at a depth of 0.5 cm beneath a patient's tissue 25, and is implanted perfectly flat. Also shown are potential positions for the external charger 150 (in dotted lines) relative to the IPG 200. A point Z marks the center of the coil 17 in the external charger, and is used generally to indicate the external charger 150's position relative to the IPG 200.

Also shown in FIG. 6 are various regions denoting the charging current received by the IPG's battery 26, Ibat. Each region reflects the resulting Ibat when the external charger 150 is moved so that point Z is located within the region. As would be expected, this empirical data shows that Ibat is highest when point Z (i.e., the external charger 150) is close and centered relative to the IPG 200, as can be seen in the inner most region where Ibat>65 mA. As point Z becomes more distant, or laterally shifts, coupling worsens, and Ibat begins to drop.

Even though an IPG 200 is usually implanted at a set depth in the patient's tissue 25 (here, 0.5 cm), and even though the external charger 150 is usually in contact with that tissue, it is useful to consider in FIG. 6 the battery charging current regions at other depths to understand charging performance when that depth varies—i.e., if the implant depth varies or if the distance between the charger and the tissue varies.

Also shown in FIG. 6 is a boundary at which $\Delta V$ equals a chosen Vt2. Although only shown in two dimensions, it will be understood that this boundary is three-dimensional, and would be shaped roughly as a hemisphere. The shaded volume within the boundary shows where $\Delta V \geq Vt2$, which defines a volume within which the external charger 150 and IPG 200 will be deemed in alignment by the alignment detector 160. Notice from the various regions within this volume that the battery charging current, Ibat~$\geq$30 mA, i.e., a suitably high current resulting in a suitably short changing session time. Should an even higher Ibat be desired (i.e., even faster charging), an even higher Vt2 could be chosen for use in the alignment detector 160, although this would reduce the volume within which good alignment would be indicated.

Returning again to FIG. 5, once Vt2 has been set, it is applied at the alignment detector 160 to determine whether $\Delta V$ is higher than Vt2, and to issue a yes/no decision to the external charger 150's control circuitry 144. Assume an application in which the external charger issues a "beep" when the external charger 150 and IPG 200 are not aligned. If some $\Delta Vx$ value is <Vt2, indicating poor coupling, the control circuitry 144 will enable the alignment indicator 162 to issue a "beep"—an alignment condition This will provide notice to the user to laterally move the external charger 150 until the beeping ceases, i.e., until some subsequent $\Delta Vx$ value is >Vt2. When $\Delta Vx$>Vt2, indicating good alignment, the control circuitry 144 will not enable the alignment indicator 162, and the external charger 150 will be silent—a no-alignment condition.

While bench test data is useful in setting Vt2 for the alignment detector 160, it should be understood that Vt2 may need to be programmed into the external charger 150 for each patient because of the particulars of each patient's IPG 200. For example, it cannot be assumed in an actual patient that the patient's IPG 200 has been implanted perfectly flat at a depth of 0.5 cm, as was assumed in FIG. 6. Instead, Vt2 may need to be tailored for each patient on the basis of experimentation. In patients having very deep implants, Vt2 may need to be set at a relatively small value, but still large enough to provide a reasonable large volume of alignment. Vt2 can also be set based on simulations or calculations. Although not shown, it should be understood that Vt2 could be experimentally determined, and programmed into the external charger 150, in any number of ways.

Figure 7:
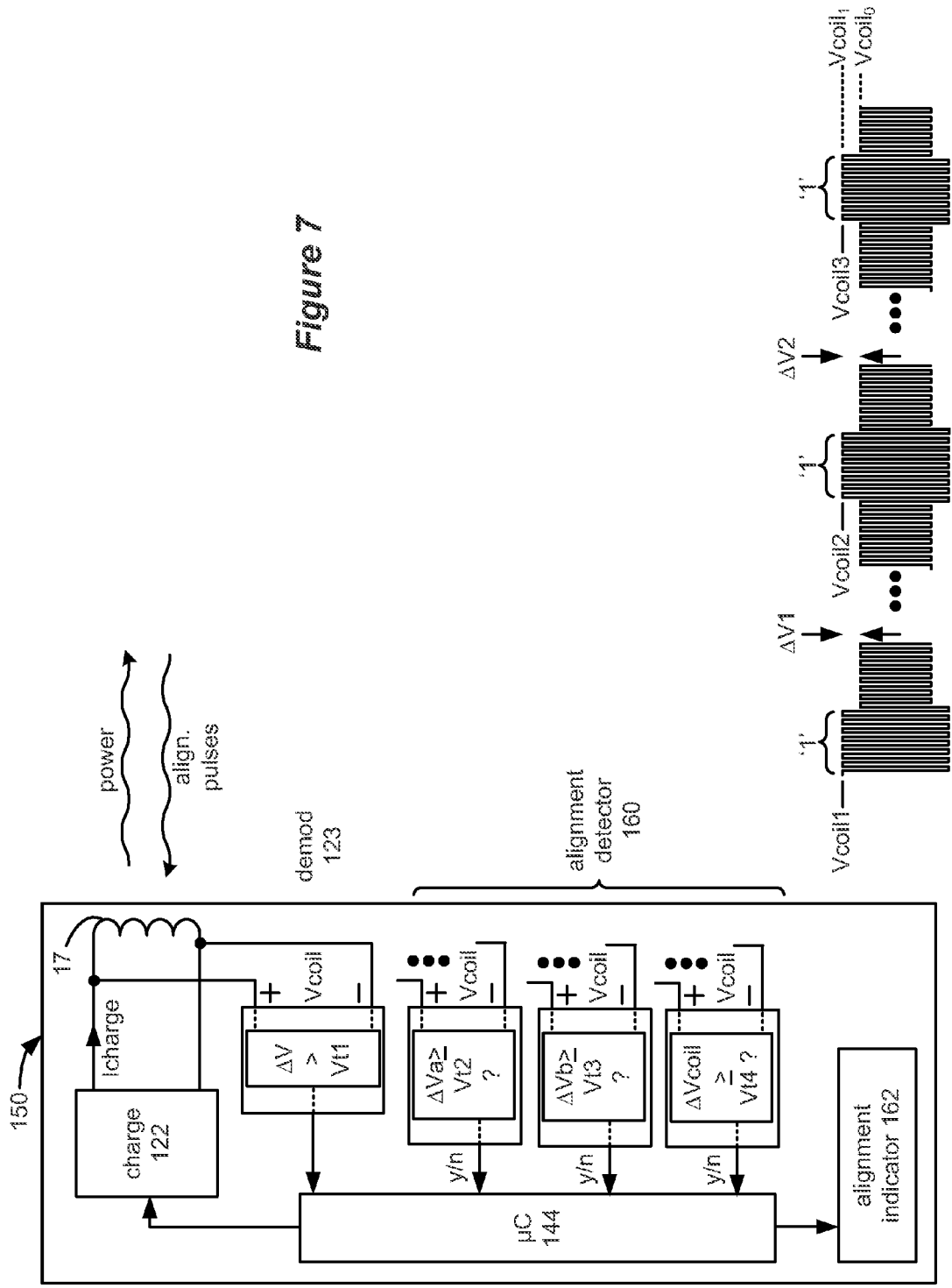
FIGS. 7 and 8 show how FIGS. 5 and 6 can be modified by using both $\Delta V$ and Vcoil thresholds to define a volume having an improved battery charge rate.
Figure 8:
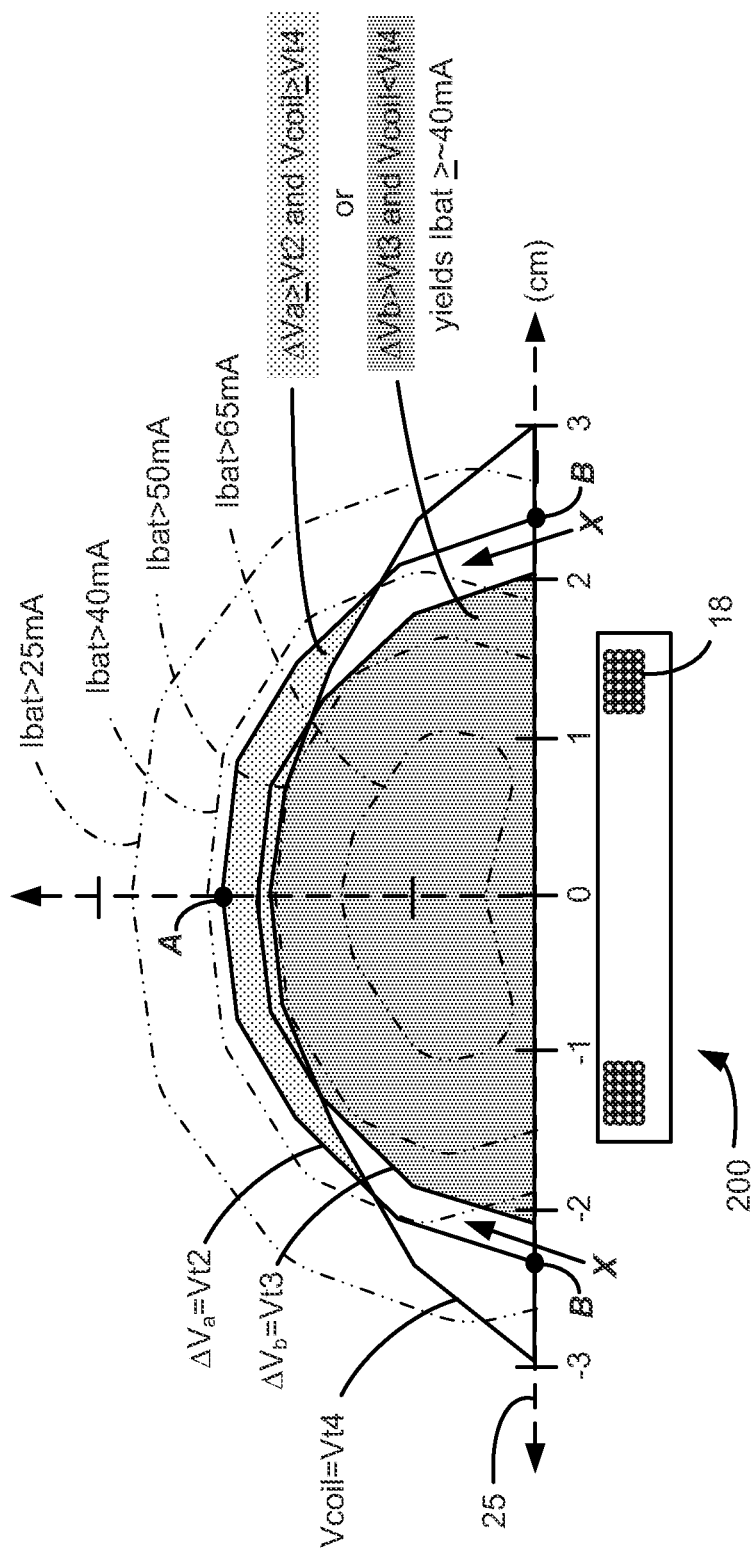

FIGS. 7 and 8 illustrate a modification to the external charger 150/IPG 200 system of FIGS. 5 and 6. In this case, the alignment volume is further refined by considering both $\Delta V$ and Vcoil thresholds at the alignment detector 160. The rationale for this modification is illustrated in FIG. 8. Consider points A and B at a $\Delta V$ boundary ($\Delta Va$), i.e., where $\Delta Va$ equals an appropriately determined Vt2 as explained earlier. Notice that at a point A, which is centered with the IPG's axis, provides a battery charging current is relatively high (Ibat~40 mA), while at lateral point B it is relatively low (Ibat~30 mA). It is clear from the various Ibat regions that such lateral regions proximate to point B generally define smaller charging current values along a constant $\Delta V$ boundary. This suggests that while $\Delta V$ can act as an indicator of coupling, it is not a perfect one. Thus, using $\Delta V$ as a sole criterion for determining alignment, while helpful, does not provide uniform charging at the alignment volume boundary.

As such, the inventors have noticed that consideration of $\Delta V$ can be combined with consideration of the actual magnitude of Vcoil at the alignment detector 160 to further refine the alignment volume to regions of higher battery charging currents, Ibat. Of course, Vcoil is an AC varying signal, and so that signal's magnitude is defined in DC terms in any conventional manner, such as by its peak voltage, its peak-to-peak voltage, its rms value, etc.

A boundary at which Vcoil equals a chosen threshold, Vt4, is superimposed on two $\Delta V$ boundaries ($\Delta Va$=Vt2; $\Delta Vb$=Vt3>Vt2) in FIG. 8. Notice that the battery charging current Ibat along this Vcoil boundary is lower in regions of poor lateral alignment. (This indicates that Vcoil itself, like $\Delta V$, is also not a perfect indicator of coupling). Unlike $\Delta V$, which decreases as distance from the IPG increases, Vcoil will generally increase as distance from the IPG increases.

The shaded volume in FIG. 8 shows an improved alignment volume imposed by more-complicated mathematical conditions, which conditions are imposed by the alignment detector 160 and/or the control circuitry 144 in this embodiment to signal alignment. The mathematical conditions are most easily understood by considering the volume in two parts, each differently shaded in FIG. 8 for easier viewing. The top part indicates an external charger 150 position where $\Delta Va > Vt2$ and $Vcoil > Vt4$. (The external charger 150 is not superimposed in FIG. 8 for clarity). The bottom portion indicates an external charger 150 position where $\Delta Vb > Vt3$ and $Vcoil < Vt4$. Satisfaction of either of these conditions will be interpreted by the control circuitry 144 as an aligned condition (hence, the 'or' in the formula in FIG. 8).

Notice that this modified alignment volume excludes notch-shaped lower-current lateral regions X otherwise included within the volume when only the $\Delta V$ threshold is considered (FIG. 6). (Again, in three dimensions this notch X would be shaped generally like a ring). Because these regions X provide lower battery charging currents, excluding them generally improves the guaranteed battery charging current to Ibat~$\geq$40 mA. Therefore, this modified volume—arrived at by considering both $\Delta V$ and Vcoil—provides for a more refined alignment volume with faster battery recharge times.

It should be noticed that this modified volume does not perfectly map to higher battery charging currents: there are still small regions inside of the volume at the lateral-most points that would provide smaller charging currents (<40 mA), and small regions outside of the volume that have suitably high current (>40 mA). Still, the probability of external charger 150 placement in these regions is small compared to the totality of the alignment volume, and such regions are therefore tolerable. Inclusion of further conditions—i.e., consideration of other $\Delta V$ and Vcoil thresholds—can be used to further sculpt the alignment volume to a more ideal shape having better correlation with the resulting battery charging currents. Such other even-more-complicated mathematical conditions relying on pluralities of $\Delta V$ and Vcoil thresholds are not shown for clarity, but should be obvious given the basic scheme that is disclosed.

Circuitry for implementing the alignment scheme of FIG. 8 is shown in FIG. 7. The alignment detector in this example can be viewed as having three separate modules: two for comparing Vcoil to the two $\Delta V$ thresholds ($\Delta Va$ and $\Delta Vb$), and one for assessing the magnitude of Vcoil. Each is shown as issuing a yes/no decision to the control circuit 144. It does not particularly matter if Vcoil is considered during provision of the alignment pulses ($Vcoil_1$) or during periods between pulses ($Vcoil_0$): $\Delta V$ is also considered, which relates $Vcoil_0$ and $Vcoil_1$, so either can be used as representative of the magnitude of Vcoil. As before, it is not necessary that the circuitry for assessing $\Delta Va$, $\Delta Vb$ and Vcoil be entirely separate in the alignment detector 160. They can wholly or in part be combined, or combined with the demodulator 123 for the LSK data, or combined with the control circuitry 144. As with the $\Delta V$ thresholds, the Vcoil threshold may be determined through experimentation, simulation, or calculations and can be programmed into the external charger 150 by known means.

Figure 9:
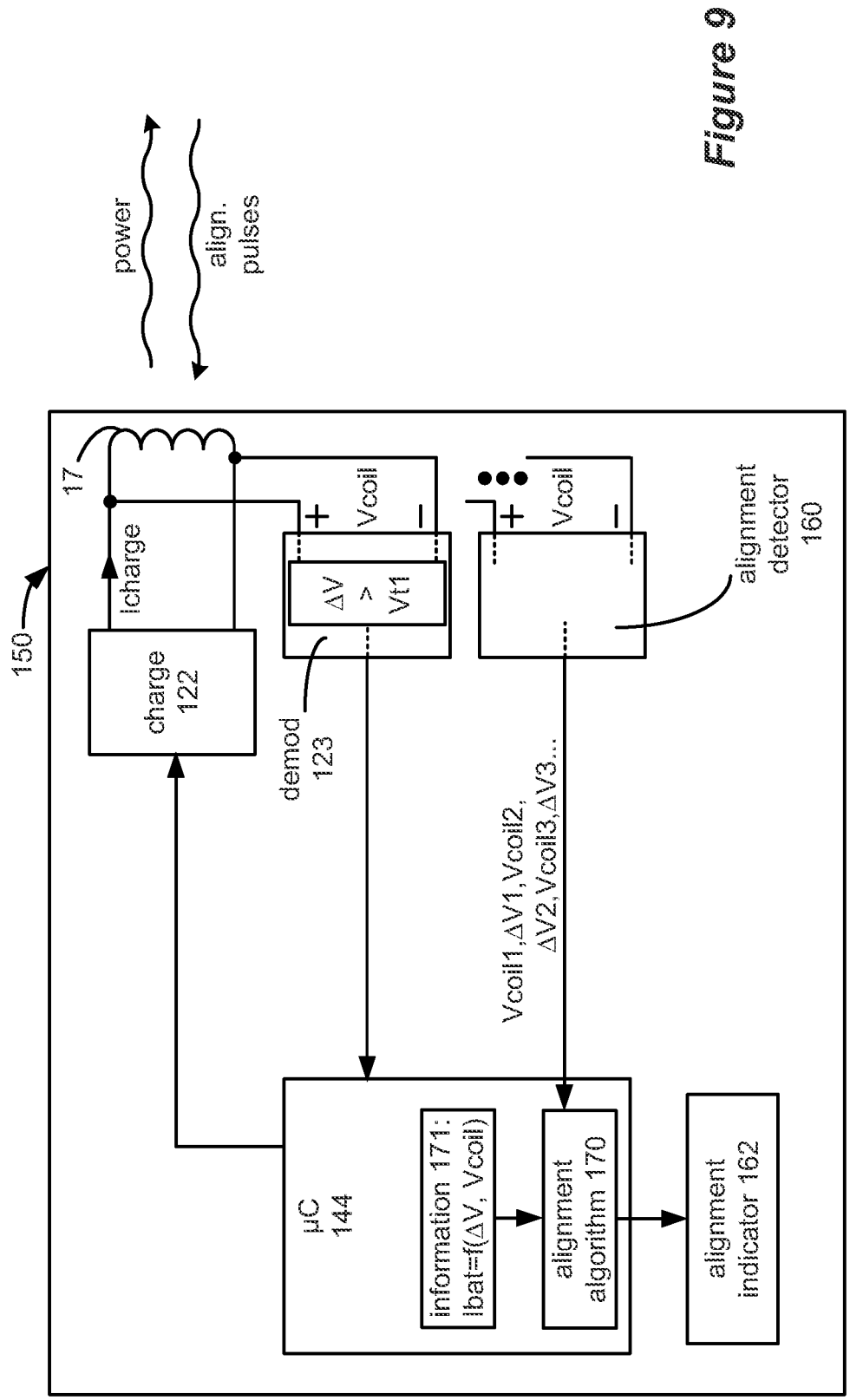
FIGS. 9 and 10 show a more generic case of an improved external charger in which $\Delta V$ and Vcoil measurements are provided to an alignment algorithm for interpretation.
Figure 10:
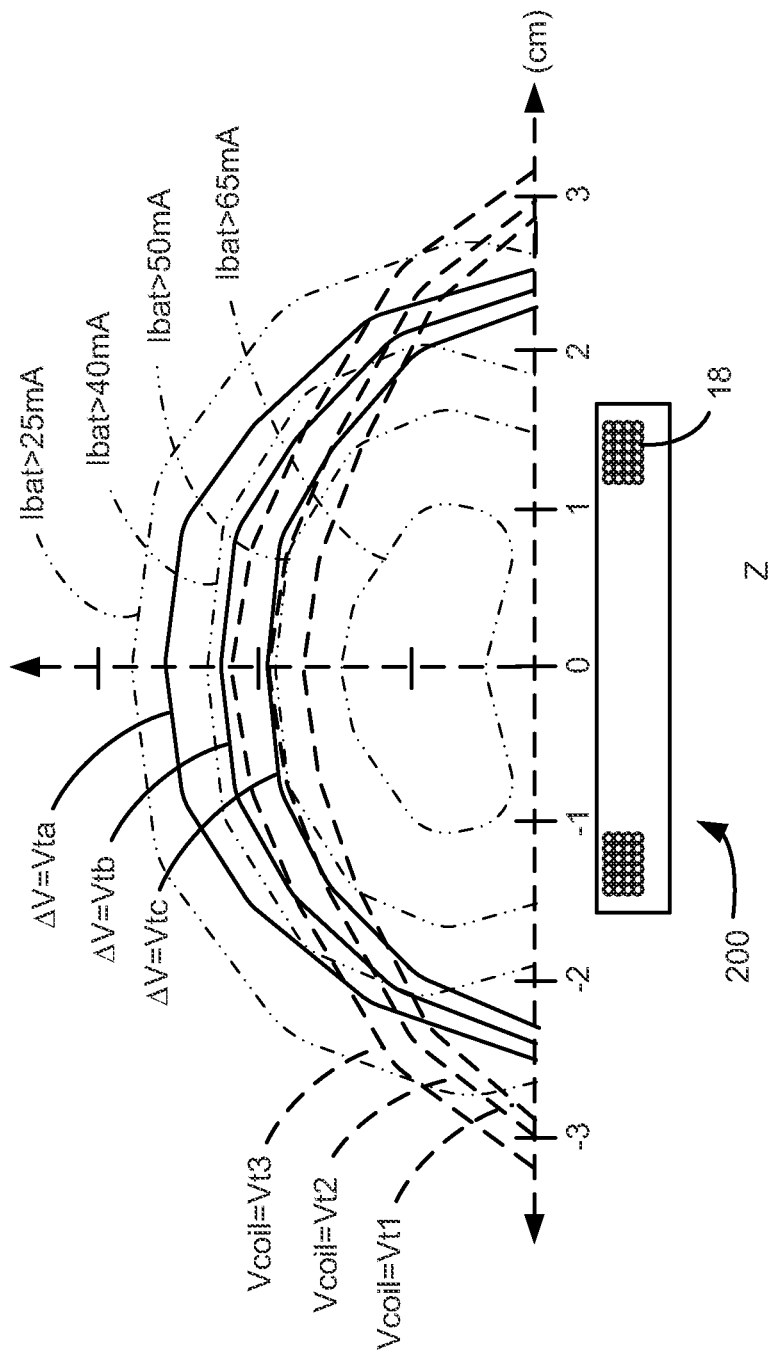

FIG. 9 illustrates yet another example of an external charger 150 for use with the disclosed alignment detection techniques. In this example, the alignment detector 160 does not provide yes/no decisions concerning $\Delta V$ (and also possibly Vcoil; see FIGS. 7 and 8) to the control circuitry 144. Instead, $\Delta V$ (and also possibly Vcoil) are sent to the control circuitry 144 which processes them, and determines alignment in accordance with an alignment algorithm 170. (The alignment detector 160 in this example could comprise an A/D converter). The alignment algorithm 170 preferably comprises software accessible by the control circuitry 144. In this example, the alignment algorithm 170 is supplied with coupling information 171 that, generally speaking, relates a coupling parameter with $\Delta V$ (and possibly also Vcoil). In the example shown, the information 171 relates the battery charging current Ibat as a function of $\Delta V$ (and possibly also Vcoil). Such information may come from families of curves, such as those shown in FIG. 10 as determined by simulation, experimentation, or calculation on an actual patient. Again, the information 171 may comprise data stored in a memory and associated with the alignment algorithm 170.

Once the $\Delta V$ (and possibly also Vcoil) data is received from the alignment detector 160, the alignment algorithm 170 can call on the information 171 to make a determination of the expected coupling between the external charger 150 and the IPG 200 at any given moment, e.g., the expected Ibat based on $\Delta V$ (and possibly also Vcoil). As before, this alignment determination can be indicated to the patient (162) so that appropriate action (moving the charger) can be taken. Alternatively, because the alignment algorithm 170 in this example determines a relative degree of alignment rather than an alignment/no-alignment determination, the alignment indicator 162 may indicate this relative amount to the patient. For example, the expect Ibat level as determined by the alignment algorithm 170 may be displayed to the patient.

Figure 11:
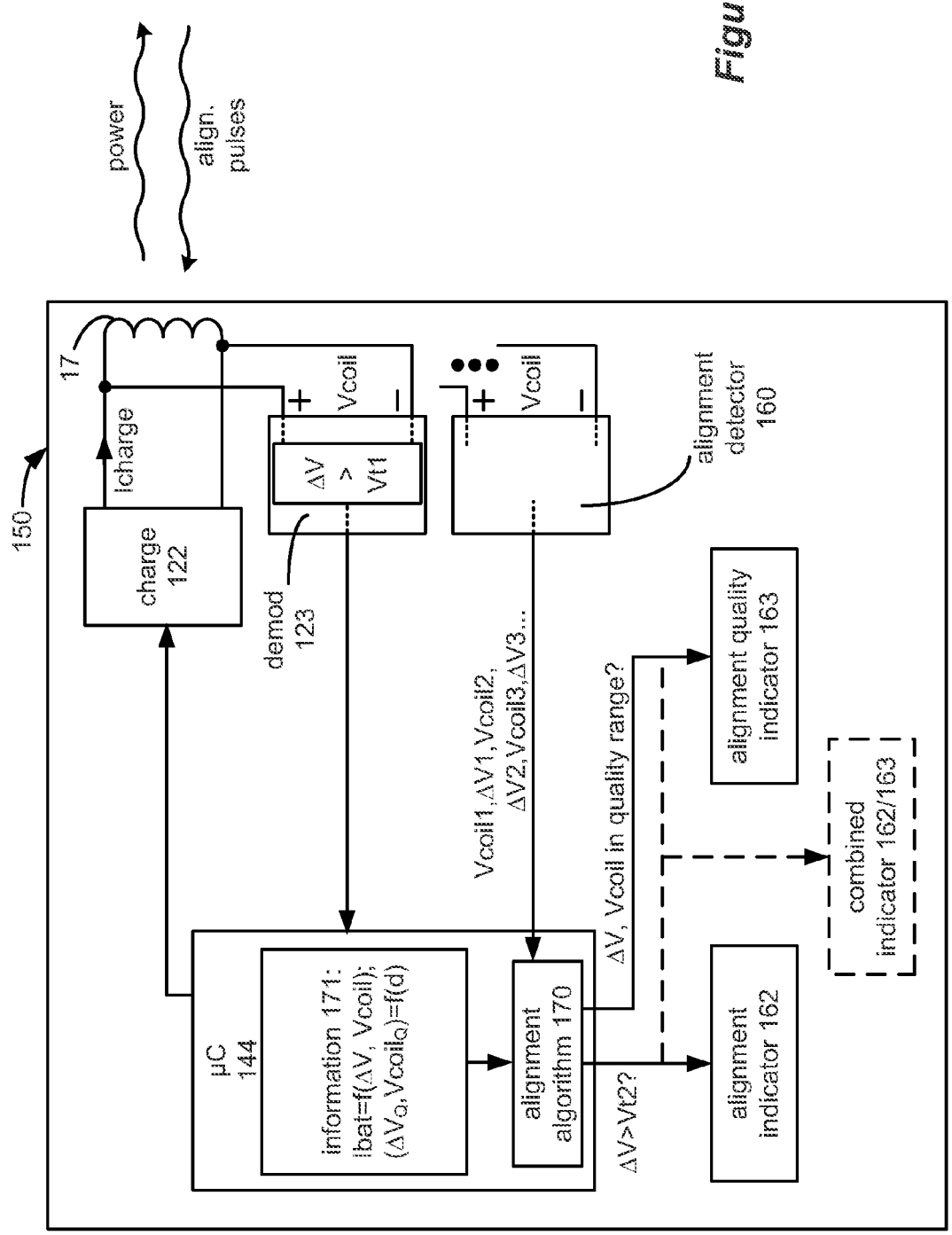
FIGS. 11 and 12 show an improved external charger in which $\Delta V$ and Vcoil measurements are used to indicate alignment quality as well as alignment.

FIG. 11 shows another example of an improved external charger 150 relying on the received $\Delta V$ and Vcoil measurements, and the information 171 stored in association with the control circuitry 144. However, in addition to indicating mere alignment via alignment indicator 162, alignment quality is also indicated to the user via another indicator 163. As will be discussed further below, such additional indication of alignment quality informs the user whether to laterally shift the position of the external charger 150 to achieve even better charging performance.

Figure 12:
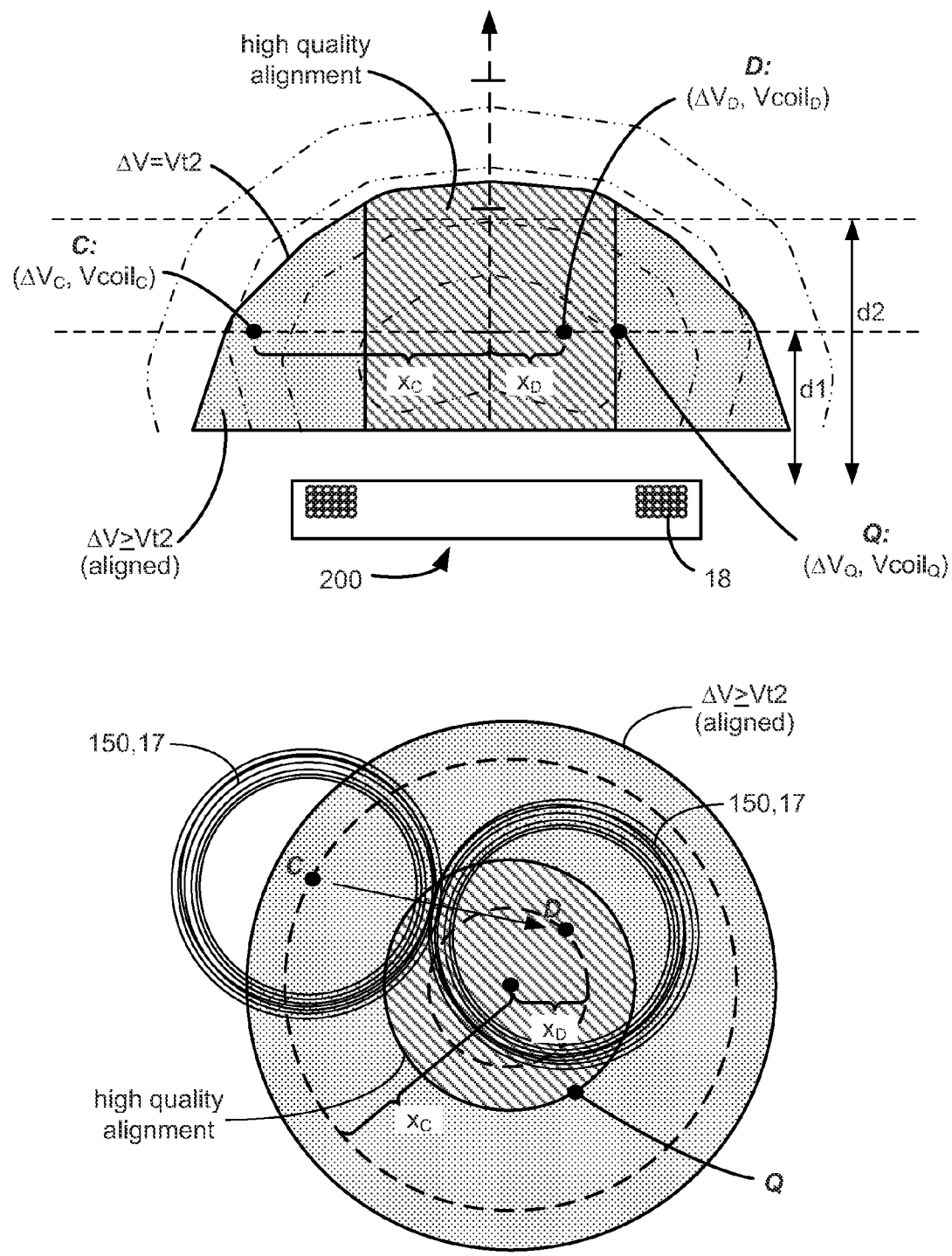

Alignment quality is illustrated in FIG. 12. As one will appreciate from the earlier illustrations depicting constant $\Delta V$ and Vcoil boundaries, these boundaries have different shapes. As such, each $\Delta V$, Vcoil pair corresponds to a particular depth, d, and lateral offset, x of the external charger 150 relative to the IPG 200. As viewed from the top down in the bottom of FIG. 12, any given $\Delta V$, Vcoil pair indicates a circle around which the external charger 150 could be positioned relative to the IPG 200. In other words, each unique $\Delta V$, Vcoil pair provides some indication of the relative position of the external charger 150 to the IPG 200, even if not the exact direction between the two. Two such positions C and D are shown in FIG. 12, each having a unique lateral offset ($x_C$, $x_D$), but both at the same depth, d1. Considering positions at the same depth is useful to discuss because, as mentioned earlier, the external charger 150 is generally placed in contact with the patient's tissue 25 (not shown in FIG. 12), and thus generally cannot be changed for a given IPG 200.

Both positions C and D for the external charger 150 shown in FIG. 12 are satisfactorily aligned with the IPG 100, as both are contained with the alignment volume defined previously in FIG. 6 (i.e., $\Delta V \geq Vt2$). (The more-complicated alignment volume of FIG. 8 could also be used, but is not shown). As such, both positions C and D would trigger alignment indicator 162 (FIG. 11) as discussed previously. Note however that position C, while aligned, isn't of the best alignment quality. It is very near the ΔV=Vt2 boundary, meaning battery charging currents could be improved, or that a small change in position could shift the external charger out of alignment. Relatively speaking, position C, although aligned, can be considered of poor alignment quality. Position D denotes a shift in the lateral position from position C, and, by contrast, has a relatively high battery charging current and high alignment quality.

The uniqueness of the position for each ΔV, Vcoil pair can be used by the alignment algorithm 170 to define a high quality alignment volume, shown as hatched in FIG. 12, which boundary occurs at position Q. In the example shown, the high quality alignment volume defines a volume of constant lateral offset relative to the axis of the IPG 200—effectively a cylinder. Although the shape of the high quality alignment volume can be changed as will be discussed further below, a generally cylindrical shape is reasonable when one considers the set depth of the IPG 200. When the IPG 200 is implanted relatively shallow (d1), and considering the hemispherical shape of the alignment volume, a larger range of lateral movement still results in adequate charging. As such, the user has reasonable leeway to laterally shift the external charger 150 to perhaps improve the alignment by shifting towards the high quality alignment volume. By contrast, when the IPG 200 is relatively deep (d2) (and assuming that the ΔV has not been adjusted), a smaller amount of lateral shifting is permissible. In such a case, even aligned positioned result in minimally-acceptable battery charging currents values because all potential aligned values are already close to the alignment boundary (ΔV=Vt2). Therefore, at large depths (d2), most or all aligned positions of the external charger 150 may need to be tolerated as high quality alignment positions, because the user could not change the quality by lateral shifting in any event.

The shape of the high quality alignment volume can be defined and applied by the alignment algorithm 170 in conjunction with information 171 (FIG. 11), which information provides quality boundary values (ΔV$_Q$, Vcoil$_Q$) for each depth. The quality boundary values are used to define the shape of the high quality alignment volume, and as mentioned earlier can be set based on experimentation, calculation, or simulation to provide a particular shape of that volume (e.g., cylindrical). The external charger 150 of FIG. 11 works as follows. As the control circuit 144 receives a ΔV, Vcoil pairs, and in particular (ΔV$_C$, Vcoil$_C$) corresponding to position C, the algorithm 170 would know the relative position (x$_C$, d1) of the external charger in a circle relative to the IPG 100. From that depth, the algorithm can compare (ΔV$_C$, Vcoil$_C$) to a quality value (ΔV$_Q$, Vcoil$_Q$) corresponding to that depth, which quality value may be stored with, or interpretable from, the information 171. In other words, the algorithm 170 can determine whether position C is within position Q at the boundary of the high quality alignment volume. If so, it can trigger the alignment quality indicator 163; if not, that indicator 163 can remain silent.

To summarize, both indicators 162 and 163 work together to inform the user about alignment during the charging process. Alignment indicator 162 indicates whether the external charger 150 is suitably aligned, a condition indicating that power provided to the implantable medical device is relatively low. Alignment quality indicator 163 further indicates the relative quality of that alignment, and whether it can be improved. For example, if both indicators 162 and 163 are active, the user will know that charging is occurring with high quality, because this condition indicates that power provided to the implantable medical device is relatively high. If indicator 162 is active but indicator 163 is not, the user can know to laterally adjust the position of the external charger 150 until the indicator 163 activates.

Note that the user may not know in which relative lateral position to move the external charger 150, but finding an improved position is not difficult as the user need merely move the charger around to random positions until the indicator 163 is engaged, in the same way that the user would move the charger to establish suitable charging in the first place. Other techniques exist in the art for indicating to a user in which direction to move a misaligned external charger to improve alignment, and such approaches can be used in combination with the disclosed techniques if necessary. See, e.g., U.S. Patent Publication 2011/0004278.

The indicators 162 and 163 will preferably provide distinct indications to the user so that the user can understand whether the external charger 150 is suitably aligned but perhaps needing some adjustment, or whether it is well alignment with good quality and can be left alone. Different tones (high pitch, low pitch) could be used. Or, a combined indicator 162/163 can receive the alignment and alignment quality data to issue an appropriate indication to the user. For example, Combined indictor 162/163 might: issue a solid tone when the external charger 150 is not aligned; issue period beeps when it is aligned but not with good quality; and be silent when it is aligned with good quality. If the external charger 150 is visible to the patient, the indicators 162 and 163 may comprise different LEDs on the charger housing, or a single LED 162/163 issuing different colors or blink rates depending on the relative alignment. Should the user interface of the external charger 150 be too simple, or too difficult to view, the alignment and quality alignment indications can be sent to another device external to the charger with a more suitable interface. For example, the indications can be sent to an external controller for the IPG 200 where they may be viewed on the external controller's display, as discussed in U.S. Patent Publication 2010/09305663, which is incorporated herein by reference.

Because the alignment quality indicator 163 can be understood as merely another type of alignment indicator 162, it should be understood that use of both types of indictors 162 and 163 in an external charger 150 is not strictly necessary. Indeed, the alignment quality indicator 163 can act as the alignment indicator 162 altogether, and can be considered as an alignment indicator.

To this point in the disclosure, it has been assumed that data-less periodic alignment pulses provide the modulation at the IPG 200 to provide the reflections at the external charger 150, i.e., the reflections from which ΔV (and possibly also Vcoil) can be assessed according to the disclosed alignment detection techniques. However, ΔV (and Vcoil) can also be gleaned using different constructs. For example, instead of assessing only alignment pulses, the alignment detector 160 could assess reflections arising from the transmission of actual LSK data, i.e., data otherwise intended for decoding at the demodulator 123. This would be a particularly useful alternative in instances where LSK data is sent from the IPG 200 with sufficient regularity to also function as a means of detecting alignment in accordance with the disclosed techniques. Periodic reporting of the battery capacity might be one such instance in which both LSK data and alignment data could be gleaned from the same reflections at the external charger 150. Moreover, even if actual LSK data is not used, constructs other than single periodic alignment pulses could also be used to produce the necessary reflections.

To this point, it has also been assumed that the coil 17 in the external charger 150 is differentially connected to the alignment detector 160, with both ends of the coil 17 being received at the alignment detector 160. However, this is not strictly necessary. Instead, a single end of the coil 17 can be received at the alignment detector 160.

It has also been assumed that the coil voltage ($\Delta V$ and/or Vcoil) is assessed to make the alignment decision, but this is not strictly necessary, and instead other electrical parameters of the coil could also be assessed. For example, in other embodiments, Vcoil produced by the charging circuitry 122 can be fixed, which would cause the charging current, Icharge, through the coil 17 to vary as the impedance of the coil 18 in the IPG 200 is modulated. The technique could therefore be modified to monitor the current through the coil ($\Delta$Icharge and/or Icoil) to make alignment determinations. Moreover, coil electrical parameters (e.g., voltage or current) could also be processed, scaled, regulated, or buffered before being presented to the alignment detector 160. Any of these means of detection comprises "assessment" of the relevant electrical parameter or its change.

It has also been assumed that the magnetic charging field is used to provide power to charge the battery 26 in the IPG 200. However, the IPG 200 need not contain a battery 26, and instead the external charger 150 can be used to provide continuous power to operate the IPG 200.

Finally, the alignment techniques disclosed herein can be used in conjunction with the above-referenced concurrently-filed application, which uses $\Delta V$ (and possibly also Vcoil) to provide closed loop charging of the IPG.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A system, comprising:
    an implantable medical device, comprising:
        a first coil configured to receive a magnetic field for providing power to the implantable medical device; and
        at least one switch configured to modulate an impedance of the first coil during receipt of the magnetic field; and
    an external charger, comprising:
        a second coil configured to produce the magnetic field;
        an alignment detector configured to measure an electrical parameter of the second coil and to assess at least a magnitude of the measured electrical parameter and a magnitude of a change in the measured electrical parameter caused by modulation of the impedance of the first coil; and
        at least one alignment indicator configured to indicate the alignment between the external charger and the implantable medical device based upon the magnitude of the measured electrical parameter and the magnitude of the change in the measured electrical parameter.

2. The system of claim 1, wherein the implantable medical device comprises two switches, wherein each of the switches grounds an end of the first coil.

3. The system of claim 1, wherein the at least one switch is coupled in series with the first coil.

4. The system of claim 1, wherein the at least one switch is periodically pulsed during receipt of the magnetic field.

5. The system of claim 1, wherein the implantable medical device further comprises a rechargeable battery, and wherein the magnetic field provides power to recharge the battery.

6. The system of claim 1, wherein the external charger further comprises a demodulator, wherein the at least one switch is responsive to data to be sent to the external charger, and wherein the demodulator demodulates the data during production of the magnetic field.

7. The system of claim 1, wherein the alignment detector determines the alignment by comparing the magnitude of the change to a threshold.

8. The system of claim 1, wherein the indicated alignment comprises either an alignment condition or a no-alignment condition.

9. The system of claim 1, wherein the indicated alignment comprises a degree of alignment between the external charger and the implantable medical device.

10. The system of claim 1, wherein the indicated alignment is either visual, audible, or tactile.

11. The system of claim 1, further comprising a memory configured to store coupling information, wherein the alignment detector uses the information to determine the alignment.

12. The system of claim 11, wherein the information comprises calculated, simulation, or experimental data indicative of a relationship between a coupling parameter and at least a magnitude of a change in the electrical parameter.

13. The system of claim 1, wherein the indicated alignment comprises either a first alignment condition or a second alignment condition.

14. The system of claim 13, wherein the first alignment condition comprises a condition for which power provided to the implantable medical device is relatively low, and wherein the second alignment condition comprises a condition for which power provided to the implantable medical device is relatively high.

15. The system of claim 1, wherein the electrical parameter comprises voltage.

16. The system of claim 1, wherein the electrical parameter comprises current.

* * * * *